United States Patent [19]
Schmieding

[11] Patent Number: 5,211,647
[45] Date of Patent: May 18, 1993

[54] INTERFERENCE SCREW AND CANNULATED SHEATH FOR ENDOSTEAL FIXATION OF LIGAMENTS

[75] Inventor: Reinhold Schmieding, Naples, Fla.

[73] Assignee: Arthrex Inc., Naples, Fla.

[21] Appl. No.: 836,721

[22] Filed: Feb. 19, 1992

[51] Int. Cl.⁵ .............................................. A61B 17/58
[52] U.S. Cl. ..................................... 606/104; 606/73; 606/96
[58] Field of Search ..................... 606/60, 62, 63, 64, 606/65, 66, 72, 73, 74, 99, 103, 104, 96, 88, 89

[56] References Cited

U.S. PATENT DOCUMENTS

| | | | |
|---|---|---|---|
| 4,259,072 | 3/1981 | Hirabayashi | 606/65 |
| 4,450,834 | 5/1984 | Fischer | 606/96 |
| 4,450,835 | 5/1984 | Ashis | 606/96 |
| 4,716,893 | 1/1988 | Fischer | 606/65 |
| 4,870,957 | 10/1989 | Goble | 606/73 |
| 4,927,421 | 5/1990 | Goble | 606/73 |
| 4,950,270 | 8/1990 | Bowman | 606/72 |
| 4,961,421 | 10/1990 | Muller | 606/180 |

*Primary Examiner*—Robert A. Hafer
*Assistant Examiner*—David J. Kenealy
*Attorney, Agent, or Firm*—Ostrolenk, Faber, Gerb & Soffen

[57] ABSTRACT

An interference screw and a cannulated sheath for fixating ligaments. A graft, attached between previously cut bone blocks, is placed under tension in a graft tunnel. The sheath has a cutout at one end such that during screw insertion, the graft is covered by the sheath and protected from the threads of the screw, while the bone to which the graft is being fixed is exposed to the threads of the screw. The screw is driven between the bone to which the graft is being fixed and a corresponding one of the bone blocks. The screw may be cannulated for insertion over a pre-positioned guide pin.

18 Claims, 4 Drawing Sheets

INTERFERENCE SCREW AND CANNULATED SHEATH FOR ENDOSTEAL FIXATION OF LIGAMENTS

BACKGROUND OF THE INVENTION

1. Field of the Invention

The present invention relates to a device for endosteal fixation of a ligament by screw insertion and, more specifically, to an interference screw and cannulated sheath.

2. Description of the Related Art

When a ligament or tendon becomes detached from a bone, surgery is usually required to resecure the ligament or tendon. Often, a substitute ligament or graft is attached to the bone to facilitate regrowth and permanent attachment. Various methods of graft attachment are known, such as staples and sutures over buttons. However, such methods often do not provide a sufficiently strong attachment to withstand the normal tensile loads to which they are subjected.

A stronger graft attachment is obtained by using an interference screw to wedge a graft bone block to the wall of a graft tunnel formed through the bone. FIG. 1 illustrates this method, in which the graft 2, with bone blocks 4,6 at each end, is pulled through a graft tunnel 8 in the tibia 10, by applying a tensile force on sutures 12 attached to leading bone block 6. The leading bone block 6 is brought forward into the femur 14 until it is fully nested in a graft tunnel in the femur. Then, with tension applied to the graft 2 via sutures 12, a driver is used to insert interference screws 16 between the bone blocks 4,6 and the graft tunnel, first in the femur and then in the tibia, as shown in FIG. 2. Although interference screw attachment by the above-described method is more secure than using staples or the like, the graft can be inadvertently cut or frayed by the sharp edges of the interference screw during insertion and after fixation.

SUMMARY OF THE INVENTION

Accordingly, it is an object of the present invention to provide an apparatus and method for screw fixation of ligament grafts which minimizes the likelihood of damage to the graft during and after fixation.

The present invention achieves the foregoing objective by providing a cylindrical cannulated sheath for protecting the ligament graft during insertion of an interference screw. The sheath is configured such that one end includes a cutout portion extending around up to one-half the circumference of the sheath, preferably one-third. The cutout enables the interference screw to be exposed to the tunnel wall of the bone during insertion, while at the same time covering the side of the screw facing the graft, thus protecting the graft from the screw threads during screw insertion. The sheath may optionally be provided with a thread-like continuous ridge on its outer surface to facilitate rotational insertion and removal of the sheath.

In one embodiment of the invention, a guide pin is used to guide the sheath. In this case, the interference screw is also cannulated and guided by the guide pin to the proper position between the graft bone block and the bone.

The screw is configured with a rounded back end (i.e. no threads are provided on the end of the screw) to prevent inadvertent cutting or fraying of the graft by the screw after the screw has been inserted. The leading end of the screw is tapered while the back end has an inverse hex-head for receiving a hex-head screwdriver. A cannulated hex-head screwdriver is used in the guide pin embodiment.

The interference screw is preferably made of titanium, although, other hard metals may be used, such as titanium alloys, stainless steel and stainless steel alloys, and certain biodegradable materials specially tailored for hardness, tensile strength, and compressive strength. The sheath is preferably made of a plastic material or other soft material capable of adequately holding the screw.

The method of the present invention includes the steps of drilling a graft tunnel through adjacent bone masses, extending a substitute ligament with bone blocks in the graft tunnel under tension between the adjacent bone masses, inserting the cannulated sheath of the present invention into the ligament tunnel at a rotational position such that the graft is covered and protected by the sheath and the bone tunnel wall is exposed by the cutout at the leading end of the sheath, inserting an interference screw into the cannula of the sheath, driving the interference screw between the tunnel wall exposed by the cutout and the bone block portion of the graft, and removing the sheath.

In another embodiment of the present invention, a guide pin is inserted in the graft tunnel before positioning the cannulated sheath. The interference screw is cannulated and is guided by the guide pin during insertion and driving of the interference screw.

In yet another embodiment, the interference screw is inserted into the cannula of the sheath before positioning the sheath, and the screw and the sheath are positioned simultaneously.

Other features and advantages of the present invention will become apparent from the following description of the invention which refers to the accompanying drawings.

DETAILED DESCRIPTION OF A PREFERRED EMBODIMENT

Figure 1:
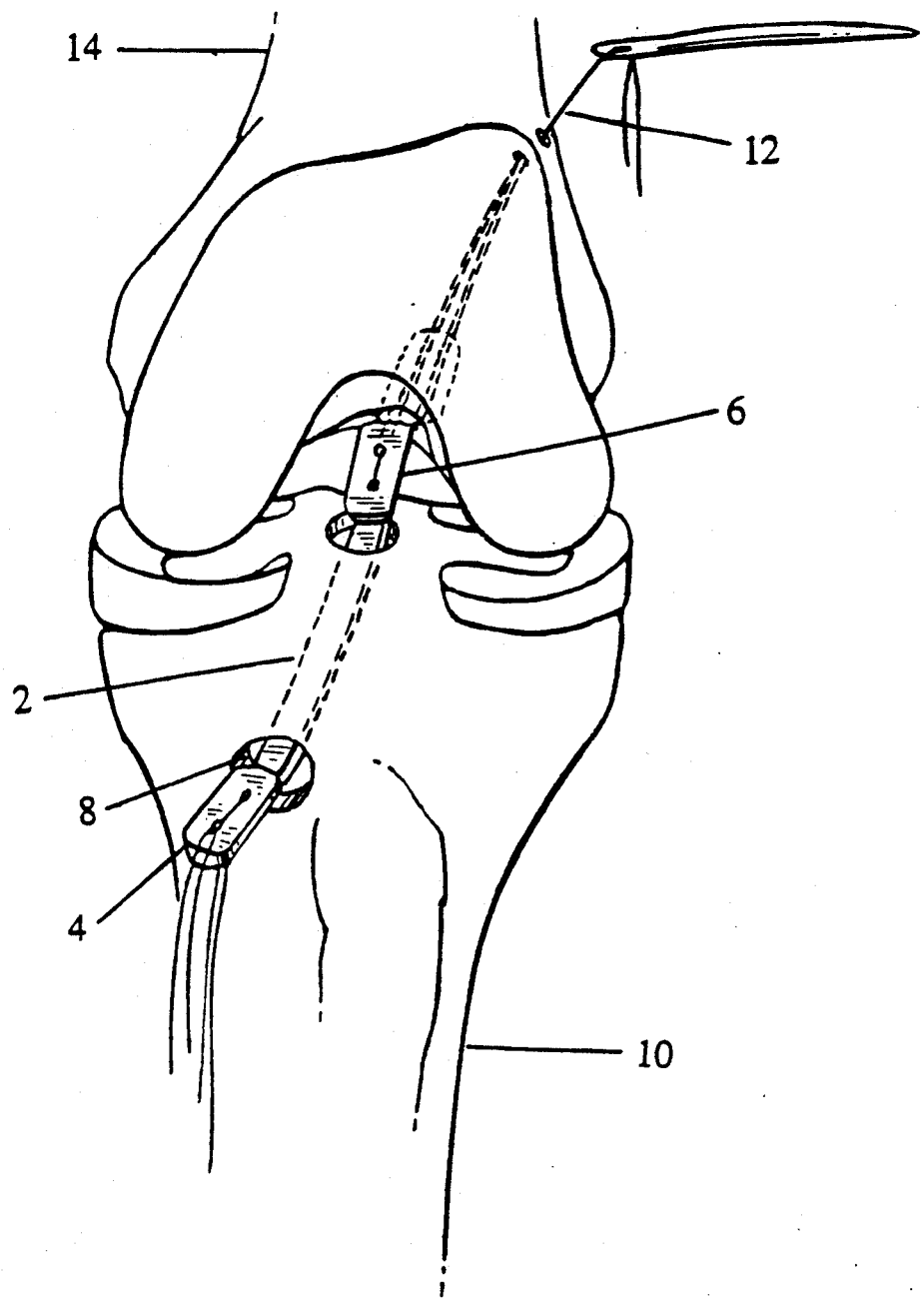
FIG. 1 shows a typical graft attached between two previously cut bone blocks being positioned in a graft tunnel.
Figure 2:
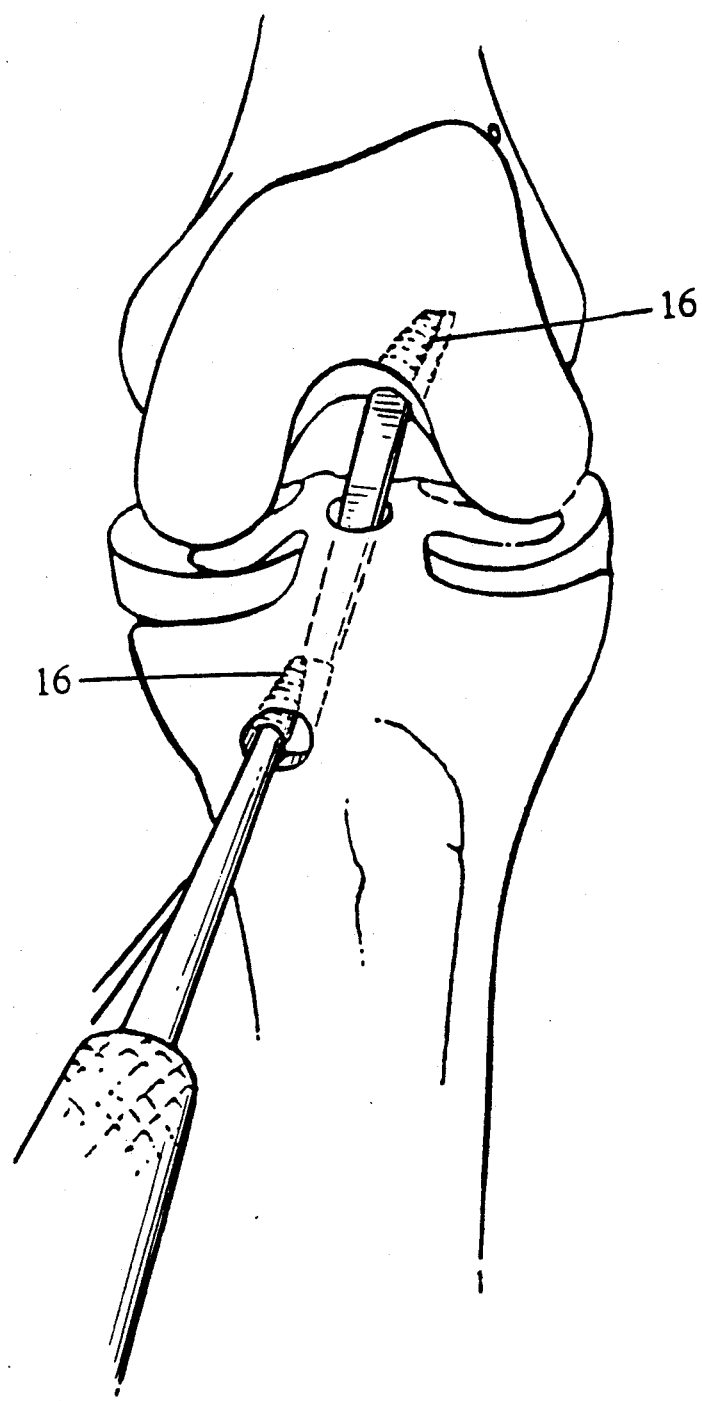
FIG. 2 shows interference screws driven between the bone masses and the corresponding bone blocks.
Figure 3:
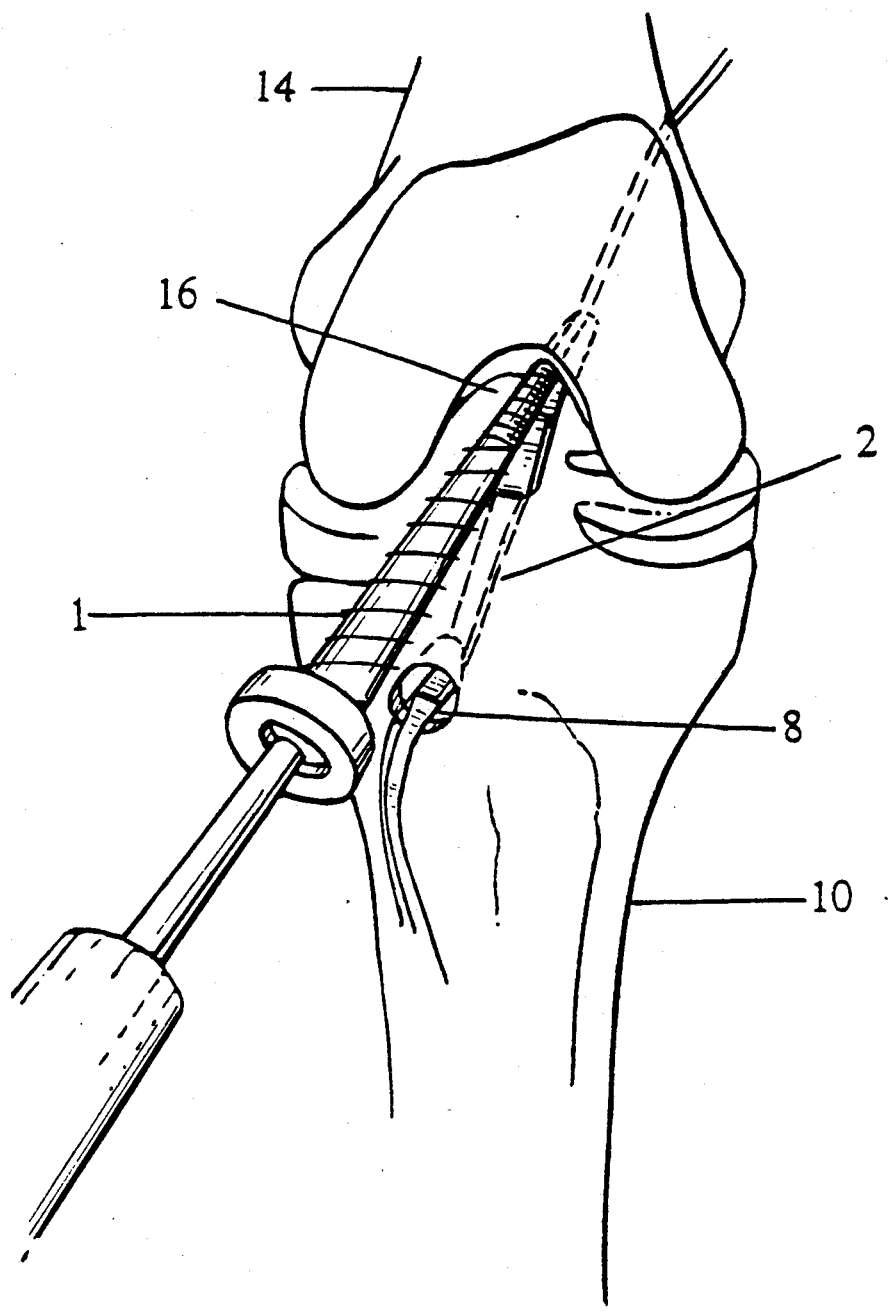
FIG. 3 shows the cannulated sheath being used to insert an interference screw in accordance with the method of the present invention.
Figure 4:
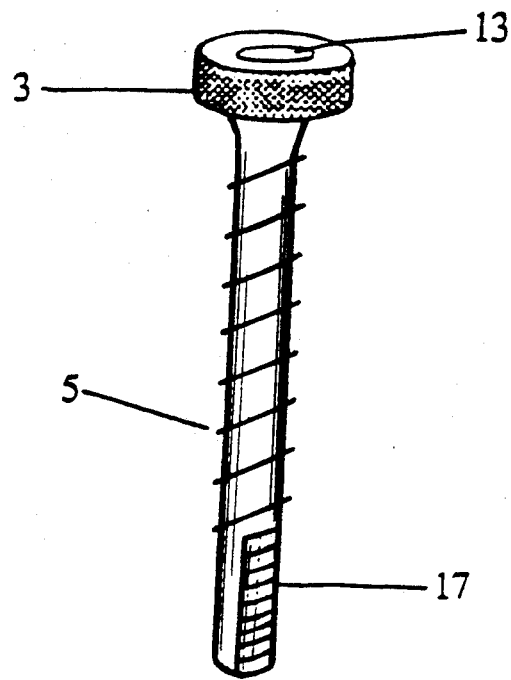
FIG. 4 shows the cannulated sheath of the present invention with the interference screw exposed by the cutout.

Referring to FIGS. 3 and 4, the present invention is a cylindrical cannulated sheath 1 which receives an interference screw 16 for use during endosteal fixation of a substitute ligament or graft 2.

The sheath 1 has a head 3 at one end and a cutout 17 at the other. The cutout 17, which extends over up to one-half of the circumference (preferably one-third) of the cylindrical sheath 1, enables the interference screw to be driven into the bone mass or tibia 10, while at the same time protecting the graft from inadvertent damage such as fraying or cutting by the screw threads 19. The sheath preferably includes a continuous thread-like ridge 5 on its outer surface, which allows the sheath to be rotated in and out of position. The sheath is preferably made of plastic.

Figure 5:
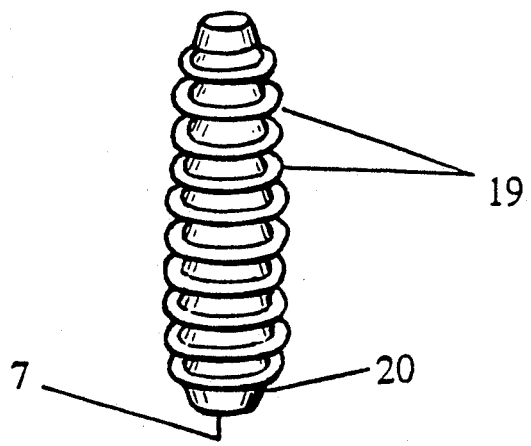
FIG. 5 shows the interference screw of the present invention.

As shown in FIG. 5, the front end of the interference screw 16 is tapered while the back end has rounded edges 20 and includes an inverse hex head 7 adapted to receive a hex head screwdriver. The rounded back edges 20 eliminate inadvertent damage to the graft after fixation.

The interference screw is preferably made of titanium, although, other hard metals may be used, such as titanium alloys, stainless steel alloys, and certain biodegradable materials specially tailored for hardness, tensile strength, and compressive strength.

Figure 6:
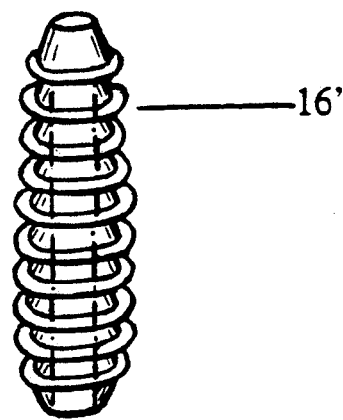
FIG. 6 shows a cannulated interference screw of an alternate embodiment of the present invention.

In an alternate embodiment as shown in FIG. 6, the interference screw 16' is cannulated for receiving a guide pin. The guide pin is positioned between the graft bone block and the femur 14 for guiding the sheath 1 and the cannulated screw 16' into position. A cannulated hex head screw driver is used to drive the cannulated screw.

The method of the invention will now be described in conjunction with FIG. 3, it being understood that endosteal fixation of a substitute ligament or graft is well known in the art. See, e.g. Kurosaka et al. "*A Biochemical Comparison of Different Surgical Techniques of Graft Fixation in Anterior Cruciate Ligament Reconstruction,*" *Am. Jour. Sports Med.*, Vol. 15, No. 3, pp. 225-229, herein incorporated by reference.

As is the usual practice in the art, a graft tunnel 8 is first drilled through the adjoining bones, in this case the tibia 10 and the femur 14. A graft 2, attached between previously cut bone blocks, preferably a patellar tendon, is extended under tension within the graft tunnel 8 between the tibia 10 and the femur 14. In the present invention, a guide pin is then hand positioned between the bone block 6 and the graft tunnel 8 adjacent the femur 14. The cannulated sheath 1 of the invention is placed over the guide pin and guided to a position such that the graft 2 is covered by the sheath 1, while the graft tunnel 8 in the femur 14 is exposed by the cutout 17. The cannulated interference screw 16' is then placed over the guide pin and inserted into the cannula 13 of the sheath. The interference screw 16' is driven into the graft tunnel 8 between the femur 14 and the bone block 6. During screw insertion, the sheath 1 covers the graft 2, thus protecting the graft from inadvertent damage that may be caused by the screw threads 19. The cannulated sheath 1 is then removed by rotation with the aid of the thread-like ridge 5, and the guide pin is removed. A similar interference screw is driven into the tibia 10 by the same process to attach the opposite end of the graft.

In an alternate embodiment, the interference screw 16 is inserted in the cannula 13 of the sheath 1 before positioning the sheath between the graft 2 and the femur 14, such that the sheath 1 and the screw 16 are positioned between the graft 2 and the femur 14 simultaneously.

The present invention provides a tight interference fit between the graft bone block 6 and the femur 14 and between the graft bone block 4 and the tibia 10, enabling early mobilization and rapid healing. Still further, the attachment provided by the present invention has superior tensile and compressive strength as well as superior effective stiffness strength as compared to other ligament replacement procedures.

The previous example is for illustrative purposes only, as the present invention is not limited to any type of ligament replacement. Those skilled in the art can certainly contemplate a variety of different procedures in which the present invention can be advantageously applied.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An apparatus for endosteal fixation of a substitute ligament by screw insertion, comprising:
   an interference screw; and
   a removable cylindrical cannulated sheath for receiving said interference screw, said sheath having a proximal end and a distal end, said distal end of said sheath having a cutout portion and a covered portion, said covered portion preventing said interference screw from damaging the substitute ligament during screw insertion, and said cutout portion exposing a portion of said interference screw to permit said interference screw to cut into a bone tunnel wall during screw insertion.

2. An apparatus according to claim 1, wherein the outer surface of said sheath has a continuous thread-like ridge to facilitate insertion and removal of said sheath into and out of position for screw insertion.

3. An apparatus according to claim 1, wherein said cutout portion extends over less than one-half of the circumference of said sheath.

4. An apparatus according to claim 3, wherein said cutout portion extends over one-third of the circumference of said sheath.

5. An apparatus according to claim 1, wherein the outer surface of said sheath has a continuous thread-like ridge to facilitate insertion and removal of said sheath into and out of position for screw insertion.

6. An apparatus according to claim 1, wherein said cannulated sheath is made of a plastic material.

7. An apparatus according to claim 1, wherein said interference screw has proximal and distal ends, said distal end being tapered and said proximal end having rounded edges.

8. An apparatus according to claim 7, wherein said proximal end has an inverse hex-head for receiving a hex-head screwdriver.

9. An apparatus according to claim 1, wherein said interference screw is cannulated for receiving a guide pin.

10. An apparatus according to claim 1, wherein said interference screw is made of titanium.

11. A method of endosteal fixation of a graft by screw insertion, comprising the steps of:
    drilling a graft tunnel through adjacent first and second bone masses;
    extending a graft attached between previously cut bone blocks under tension in said graft tunnel between said adjacent bone masses;
    positioning a cannulated sheath between said graft and said first bone mass, said cannulated sheath having a cutout at one end, said sheath being positioned such that said graft is covered by said sheath and said first bone mass is exposed by said cutout;

inserting said interference screw in the cannula of said cannulated sheath;

driving said interference screw between said first bone mass exposed by said cutout and a corresponding one of said bone blocks; and removing said cannulated sheath.

12. A method according to claim 11, wherein said cannulated sheath has a thread-like ridge on its outer surface, and wherein said removing step comprises the step of rotating said cannulated sheath, said thread-like ridge facilitating removal of said sheath upon rotation.

13. A method according to claim 11, wherein said interference screw is inserted in the cannula of said sheath before positioning said sheath between said graft and said bone mass such that said sheath and said screw are positioned between said graft and said first bone mass simultaneously.

14. A method according to claim 11, wherein said interference screw has an inverse hex-head for receiving a hex-head screwdriver, said interference screw being driven by said hex-head screwdriver.

15. A method of endosteal fixation of a graft by screw insertion, comprising the steps of:

drilling a graft tunnel through adjacent first and second bone masses;

extending a graft attached between previously cut bone blocks under tension in said graft tunnel between said adjacent bone masses;

positioning a guide pin between said graft tunnel at said first bone mass and a corresponding one of said bone blocks;

placing a cannulated sheath over said guide pin, said guide pin guiding said sheath to a position between said graft and said first bone mass, said sheath having a cutout at one end, said sheath being positioned such that said graft is covered by said sheath and said first bone mass is exposed by said cutout;

placing a cannulated interference screw over said guide pin, said guide pin guiding said screw as it is inserted through the cannula of said cannulated sheath to a position where said first bone mass is exposed by said cutout;

driving said cannulated interference screw between said first bone mass exposed by said cutout and said corresponding bone block; and removing said cannulated sheath.

16. A method according to claim 15, wherein said cannulated sheath has a thread-like ridge on its outer surface, and wherein said cannulated sheath is removed by rotating said cannulated sheath, said thread-like ridge facilitating removal of said sheath upon rotation.

17. A method according to claim 15, wherein said cannulated interference screw is inserted in the cannula of said sheath before positioning said cannulated sheath between said graft and said first bone mass, such that said sheath and said screw are positioned between said graft and said first bone mass simultaneously.

18. A method according to claim 15, wherein said cannulated interference screw has an inverse hex-head for receiving a cannulated hex-head screwdriver, said cannulated interference screw being driven by said cannulated hex-head screwdriver.

* * * * *